US00PP18163P2

(12) United States Plant Patent
Verschoor

(10) Patent No.: US PP18,163 P2
(45) Date of Patent: Oct. 30, 2007

(54) ***PHLOX* PLANT NAMED 'CANDY FLOSS'**

(50) Latin Name: *Phlox paniculata*
Varietal Denomination: Candy Floss

(75) Inventor: Jan Verschoor, Haarlem (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/454,068

(22) Filed: Jun. 15, 2006

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent Bell
(74) *Attorney, Agent, or Firm*—C. A Whealy

(57) ABSTRACT

A new and distinct cultivar of *Phlox* plant named 'Candy Floss', characterized by its upright and compact plant habit; freely basally branching habit; dense and bushy growth habit; attractive dark pink-colored flowers; freely and continuous flowering habit; resistance to Powdery Mildew; and good garden performance.

1 Drawing Sheet

Botanical designation: *Phlox paniculata.*
Cultivar denomination: 'Candy Floss'.

BACKGROUND OF THE INVENTION

The present invention relates to a new and distinct cultivar of *Phlox,* botanically known as *Phlox paniculata* and hereinafter referred to by the name 'Candy Floss'.

The new *Phlox* is a product of a planned breeding program conducted by the Inventor in Haarlem, The Netherlands. The objective of the breeding program was to create new compact *Phlox* cultivars with attractive flower coloration and Powdery Mildew resistance.

The new *Phlox* originated from a cross-pollination made by the Inventor in 1988 in Haarlem, The Netherlands, of two unidentified selections of *Phlox paniculata,* not patented. The new *Phlox* was discovered and selected by the Inventor as a single flowering plant within the progeny of the stated cross-pollination in a controlled environment in Haarlem, The Netherlands in 1999.

Asexual reproduction of the new *Phlox* by vegetative cuttings in a controlled environment in Haarlem, The Netherlands since 1999, has shown that the unique features of this new *Phlox* are stable and reproduced true to type in successive generations.

SUMMARY OF THE INVENTION

The cultivar Candy Floss has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Candy Floss'. These characteristics in combination distinguish 'Candy Floss' as a new and distinct cultivar of *Phlox:*

1. Upright and compact plant habit.
2. Freely basally branching habit; dense and bushy growth habit.
3. Attractive dark pink-colored flowers.

4. Freely and continuous flowering habit.
5. Resistant to Powdery Mildew.
6. Good garden performance.

Compared to plants of the parent selections, plants of the new *Phlox* are more compact and differ in flower coloration.

Plants of the new *Phlox* can also be compared to plants of the cultivar Little Princess, disclosed in U.S. Plant Pat. No. 13,742. In side-by-side comparisons conducted in Haarlem, The Netherlands, plants of the new *Phlox* and the cultivar Little Princess differed primarily in flower color as plants of the cultivar Little Princess had pink-colored flowers. In addition, plants of the new *Phlox* were more resistant to Powdery Mildew than plants of the cultivar Little Princess.

BRIEF DESCRIPTION OF THE PHOTOGRAPH

The accompanying colored photograph illustrates the overall appearance of the new *Phlox,* showing the colors as true as it is reasonably possible to obtain in colored reproductions of this type. Colors in the photograph may differ slightly from the color values cited in the detailed botanical description which accurately describe the colors of the new *Phlox.* The photograph comprises a side perspective view of a typical flowering plant of 'Candy Floss' grown in an outdoor nursery.

DETAILED BOTANICAL DESCRIPTION

The aforementioned photograph and following observations, measurements and values describe plants grown in Haarlem, The Netherlands, under commercial practice during the summer in an outdoor nursery with day temperatures ranging from 18° C. to 32° C. and night temperatures ranging from 10° C. to 18° C. Plants were grown for about one year when the photograph and description were taken. In the following description, color references are made to The Royal Horticultural Society Colour Chart, 2001 Edition, except where general terms of ordinary dictionary significance are used.

Botanical classification: *Phlox paniculata* cultivar Candy Floss.

Parentage:

*Female, or seed, parent.*—Unidentified selection of *Phlox paniculata,* not patented.

*Male, or pollen, parent.*—Unidentified selection of *Phlox paniculata,* not patented.

Propagation:

*Type.*—By vegetative cuttings.

*Time to produce a rooted plant.*—About four weeks.

*Root description.*—Fine; white in color.

Plant description:

*Plant form/habit.*—Upright and compact plant habit; narrow inverted triangle; moderately vigorous growth habit. Freely basally branching habit; dense and bushy growth habit.

*Plant height.*—About 42 cm.

*Plant width* (*spread*).—About 38 cm.

*Lateral branches.*—Length: about 29.5 cm. Diameter: About 3 mm. Internode length: About 3.5 cm. Strength: Strong. Texture: Smooth, glabrous. Color: 144A.

Foliage description:

*Arrangement.*—Opposite, simple.

*Length.*—About 7.3 cm.

*Width.*—About 2.6 cm.

*Shape.*—Elliptic to obovate.

*Apex.*—Acuminate.

*Base.*—Attenuate.

*Margin.*—Finely serrate.

*Texture, upper and lower surfaces.*—Smooth, glabrous.

*Venation pattern.*—Pinnate.

*Color.*—Developing leaves, upper surface: 143A. Developing leaves, lower surface: 143A to 143B. Fully expanded leaves, upper surface: 137A; venation, 144A to 144B. Fully expanded leaves, lower surface: 137C to 137D; venation, 144C to 144D.

*Petiole.*—Length: About 1 mm. Diameter: About 3 mm. Texture, upper and lower surfaces: Smooth, glabrous. Color, upper and lower surfaces: 144B.

Flower description:

*Flower type/habit.*—Single rotate and salverform flowers arranged in terminal panicles; flowers face upright and outward. Panicles conical in shape. Freely flowering habit with about 90 flower buds and flowers per inflorescence.

*Fragrance.*—Faint to moderate; spicy.

*Natural flowering season.*—Continuously flowering from July through August in Haarlem, The Netherlands. Flowers not persistent.

*Postproduction longevity.*—Flowers last about ten days on the plant.

*Flower buds.*—Height: About 2.3 cm. Diameter: About 5 mm. Shape: Obovate. Color: 63A; towards the base, 59B.

*Inflorescence height.*—About 12.5 cm.

*Inflorescence diameter.*—About 15.9 cm.

*Flower diameter.*—About 2.8 cm.

*Flower depth.*—About 2.6 cm.

*Petals.*—Quantity per flower: Typically five in a single whorl; petals fused at the base into a narrow tube. Length: About 3.1 cm. Lobe width: About 1.7 cm. Shape: Spatulate. Apex: Rounded to emarginate. Margin: Entire. Texture, upper and lower surfaces: Smooth, glabrous. Color: Developing petals, upper surface: Slightly more purple than 52A; towards the base, N57A; throat, 72B. Developing petals, lower surface: 54B; tube, 72A. Fully expanded petals, upper surface: N57A to N57B; towards the base, 58A; throat, 72B. With development, color becoming closer to N57C; towards the base, N77D; throat, 72B. Fully expanded petals, lower surface: 55B to 55C; tube, 72A.

*Sepals.*—Quantity per flower: Typically five in a single whorl, fused; narrow tubular calyx. Length: About 8 mm. Width: About 1.5 mm. Calyx shape: Campanulate. Apex: Narrowly apiculate. Margin: Entire. Texture, upper and lower surfaces: Smooth, glabrous. Color, developing sepals, upper and lower surfaces: Towards the base, 144B to 144C; towards the apex, 147A. Color, fully expanded sepals, upper and lower surfaces: Towards the base, 144A; towards the apex, 146A.

*Peduncles.*—Length: About 8.3 cm. Diameter: About 2 mm. Angle: Erect to about 45° from vertical. Strength: Strong. Texture: Smooth, glabrous. Color: 143A.

*Pedicels.*—Length: About 4 mm. Diameter: About 1 mm. Angle: About 20° to about 40° from vertical. Strength: Strong. Texture: Smooth, glabrous. Color: 143A to 143B.

*Reproductive organs.*—Stamens: Quantity per flower: Typically five; fused with petals in tube. Filament length: About 2 mm. Anther shape: Oblong. Anther length: About 2 mm. Anther color: 4D. Pollen amount: Scarce. Pollen color: 4C to 4D. Pistils: Quantity per flower: One. Pistil length: About 2.1 cm. Stigma shape: Three-parted. Stigma color: 150D. Style length: about 1.9 cm. Style color: 149B to 149C. Ovary color: 143A.

*Seed/fruit.*—Seed and fruit development have not been observed.

Disease/pest resistance: Plants of the new *Phlox* have been noted to be resistant to Powdery Mildew. Plants of the new *Phlox* have not been noted to be resistant to other pathogens and pests common to *Phlox.*

Garden performance: Plants of the new *Phlox* have been observed to have good garden performance and tolerate rain, wind and are winter hardy in The Netherlands.

It is claimed:

1. A new and distinct *Phlox* plant named 'Candy Floss' as illustrated and described.

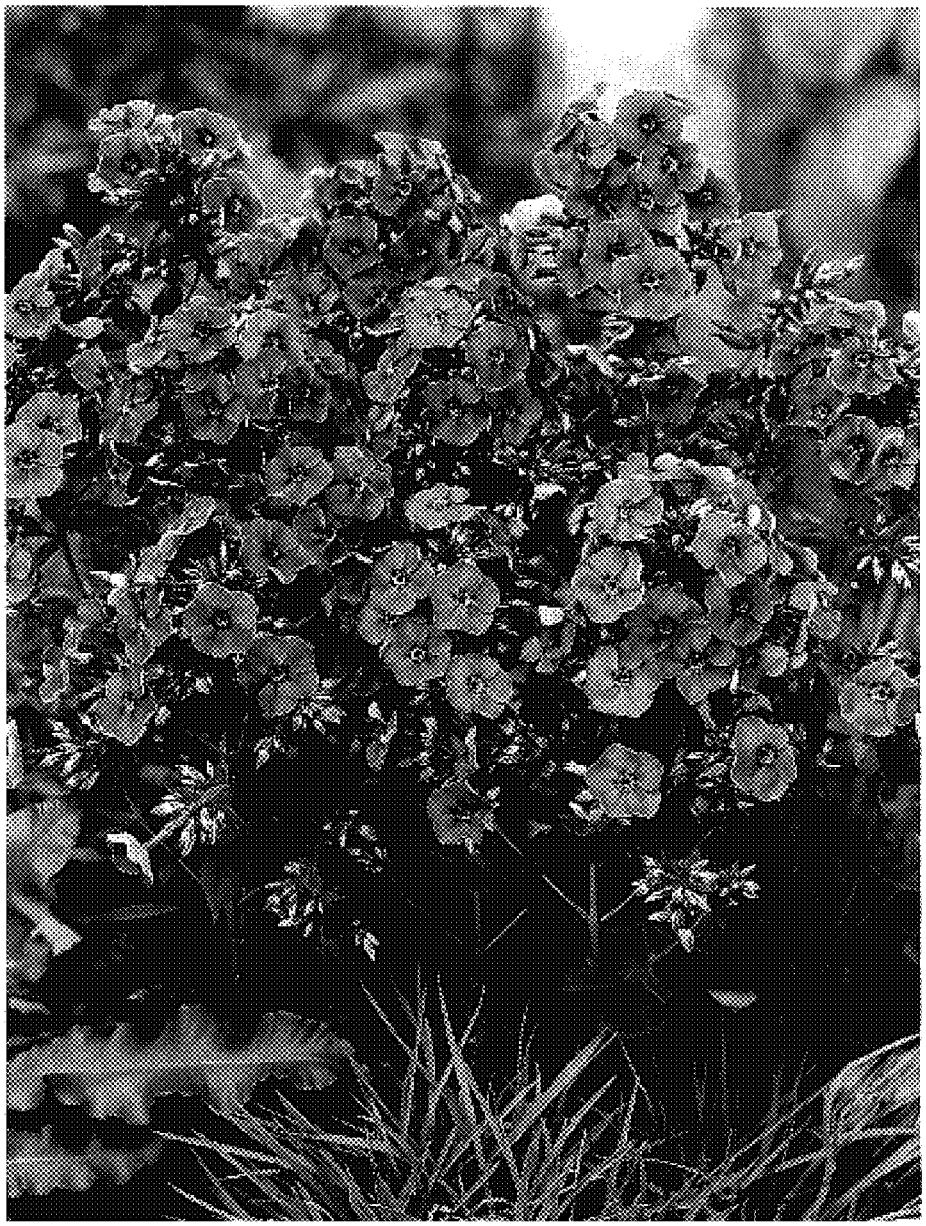

* * * * *